United States Patent [19]

Lenz et al.

[11] Patent Number: 4,732,848

[45] Date of Patent: Mar. 22, 1988

[54] PROCESS FOR THE DETERMINATION OF AN IMMUNOLOGICALLY-BINDABLE SUBSTANCE INVOLVING A FAB FRAGMENT

[75] Inventors: Helmut Lenz; Gerd Kleinhammer, both of Tutzing, Fed. Rep. of Germany

[73] Assignee: Boehringer Mannheim GmbH, Mannheim-Waldhof, Fed. Rep. of Germany

[21] Appl. No.: 767,503

[22] Filed: Aug. 20, 1985

[30] Foreign Application Priority Data

Aug. 22, 1984 [DE] Fed. Rep. of Germany ....... 3430905

[51] Int. Cl.$^4$ .............................................. G01N 33/53
[52] U.S. Cl. ............................................. 435/7; 435/25; 435/28; 436/548; 436/512; 436/513; 436/543; 436/547
[58] Field of Search ...................... 436/512, 513; 435/7

[56] References Cited

U.S. PATENT DOCUMENTS

| | | |
|---|---|---|
| 3,940,475 | 2/1976 | Gross . |
| 4,235,869 | 11/1980 | Schwarzberg . |
| 4,298,593 | 11/1981 | Ling .................................... 436/512 |
| 4,361,647 | 11/1982 | Remington . |
| 4,423,143 | 12/1983 | Rubenstein . |
| 4,444,878 | 4/1984 | Paulus ................................. 436/512 |
| 4,544,640 | 10/1985 | Soma .................................. 436/512 |

FOREIGN PATENT DOCUMENTS 2323467 11/1973 Fed. Rep. of Germany .
2743444 12/1980 Fed. Rep. of Germany .

OTHER PUBLICATIONS

Clinical Chemistry, Band 28, Nr. 12, Dec. 1982, Seiten 2408–2411, Washington, U.S.; K. Miyai et al, "Enzyme Immunoassay of Thyroxin–Binding Globulin".

Primary Examiner—Sam Rosen
Attorney, Agent, or Firm—Felfe & Lynch

[57] ABSTRACT

The present invention provides a process for the determination of an immunologically-bindable substance by immunochemical methods in heterogeneous phase, wherein (a) a sample solution containing the substance to be determined is incubated with
(b) a solid phase-bound antibody against the bindable substance to be determined
(c) a conjugate of the bindable substance to be determined and a Fab fragment of an antibody directed against a determinable enzyme in a definite amount and
(d) the enzyme which corresponds to the antibody contained in the conjugate (c), the phases are separated and the enzyme activity is measured in one of the two phases.

The present invention also provides a reagent for the determination of an immunologically-bindable substance, wherein it contains a solid phase-bound antibody against the bindable substance to be determined, a conjugate of the bindable substance to be determined and a Fab fragment of an antibody directed against a determinable enzyme, a determinable enzyme which binds immunologically with the Fab fragment contained in the conjugate and buffer.

6 Claims, No Drawings

PROCESS FOR THE DETERMINATION OF AN IMMUNOLOGICALLY-BINDABLE SUBSTANCE INVOLVING A FAB FRAGMENT

The present invention is concerned with a process for the determination of an immunologically-bindable substance by immunochemical methods in heterogeneous phase and a reagent suitable for this purpose.

The development of the immune test, starting from the radioimmune process (RIA), has led to a decisive improvement of the sensitivity and selectivity of the determination of antigen-active substances, such as proteins and haptens, and, especially in clinical-chemical laboratories, has achieved great importance. By means of the further development of these methods, besides an extension of the labelling methods available, in the case of which, besides a radioactive labelling in particular an enzyme labelling (EIA) has achieved especial importance, the development of the reaction techniques has also been differentiated considerably. Thus, not only homogeneous tests but also tests taking place in the heterogeneous phase have been developed although, in the case of the latter, the separation of solid and liquid phase, which is, as a rule, necessary, can lead to carry over and dilution problems.

In the case of processes in the heterogeneous phase, as a rule, one of the components of an immunological binding reaction is present bound to a solid phase which permits, following the corresponding binding reaction, a separation of its binding component from the liquid phase.

In the case of such processes carried out in a heterogeneous phase, use is frequently made of a competing reaction between the substance to be determined and a definite amount of a labelled derivative of the substance to be determined. The labelled derivative is thereby fixed to the solid phase in an amount which is the smaller, the greater is the amount of reaction component to be determined competing for the binding places. The labelling in the derivative competing for the binding site can thereby be radioactive or optically active but frequently a labelling by a particular enzyme is preferred. This preference is due to the fact that a determination of this labelling enzyme can be carried out without great expense for apparatus such as is necessary in the case of radioactive labelling and in the case of many optical labellings and such methods of enzyme determination have already been automated to a very large extent.

However, a substantial disadvantage of such processes using a determinable enzyme as marker is the fact that it is hereby necessary covalently to attach the enzyme, which gives rise to a number of disadvantages. Thus, in the case of the covalent reaction of an enzyme, a considerable part of its activity is frequently lost, which gives rise to considerable costs. On the other hand, such methods of binding are delicate and often difficult to carry out. As a rule, the purification conditions are thereby especially problematical since, as a rule, they include an affinity chromatographic purification. However, under the conditions necessary for the elution, a part of the enzyme activity is again destroyed, for example by low pH values.

Therefore, it is an object of the present invention to overcome the above described disadvantages of the known processes and to provide an immunological method of determination in heterogeneous phase in the case of which the advantages of an enzyme labelling are combined with the advantages of the comparatively insensitive radioactive or optical labelling.

Thus, according to the present invention, there is provided a process for the determination of an immunologically bindable substance, preferably of a hapten, by immunochemical methods in heterogeneous phase, wherein (a) a sample solution containing the substance to be determined is incubated with
(b) a solid phase-bound antibody against the bindable substance to be determined
(c) a conjugate of the bindable substance to be determined and a Fab fragment of an antibody directed against a determinable enzyme in a definite amount and
(d) the enzyme which corresponds to the antibody contained in the conjugate of (c), the phases are separated and the enzyme activity is measured in one of the two phases.

It is of importance for the present invention to use a native enzyme as labelling in combination with a conjugate from a Fab fragment of the corresponding antienzyme-antibody with the bindable substance to be determined. This conjugate competes with the free immunologically bindable substance contained in the solution to be investigated and to be determined for the solid phase-bound antibody.

As solid phase-bound antibodies against the bindable substance to be determined, there can be used not only complete polyclonal or monoclonal antibodies but also fragments thereof. The solid phase to which this antibody is bound can be present in compact form or in particulate form. As carrier materials, there can be used all substances to which biological proteins can be bound with maintenance of their biological activity, such substances being well known in large numbers. Most frequently, they are glasses, synthetic resins or synthetic or natural polymers, for example celluloses, dextrans, styrene polymers and the like. Ion exchangers and non-specific adsorbers can also be used. The binding of the antibody to the carrier material can take place by adsorption, covalent binding, via ionic bondings, by polymerisation, by cross-linking and the like, all these processes being well known. In the case of a polyvalent antibody, this can also be fixed on to the carrier material by immunological precipitation.

As further reagent, the present invention uses a conjugate of the bindable substance to be determined, preferably a hapten, and a Fab fragment of an antibody which is directed against the determinable enzyme to be used in the determination process. These antienzyme-Fab fragments can be either monoclonal, i.e. obtained in the cell culture, or are obtained in conventional manner by immunising animals against the determination enzyme and obtaining the antibodies formed, for example by means of affinity chromatography and clearing, for obtaining the Fab fragments. Methods which can be used for this purpose are described, for example, by Alan Johnstone and Robin Thorpe in "Immunochemistry in Practice", pub. Blackwell Scientific Publications, 1982, Oxford.

The linking of the antienzyme-Fab fragments thus obtained with the substance to be determined, for example a hapten, also takes place by the methods known for this purpose, for example with the use of difunctional bridge builders, such as active esters, dialdehydes and the like.

The enzyme used according to the present invention can be any determinable enzyme. Preferably, there are used enzymes which have proved to be useful in enzyme immuno assays which, as a rule, are characterised by stability, ready availability and simple determination. Typical examples of such enzymes include peroxidase, alkaline phosphatase, β-galactosidase, glucoamylase, glucose oxidase, acetylcholineesterase, catalase, lysozyme, malate dehydrogenase, glucose-6-phosphate dehydrogenase and β-amylase, peroxidase and β-galactosidase being especially preferred.

Admittedly, a process is already known (see Z. med. Labor.-Diagn., 25, 196 et seq./1984) in which antibody chimeras are used which arise by linking complete antibodies with different antigen specificity. Those antibody chimeras are thereby considered which consist of an antigen-specific and an enzyme-specific antibody. However, in the case of the use of such antibody chimeras, it would be necessary to carry out the measurement of a marking enzyme on the solid phase since such a chimera precipitates the enzyme and thus binds to the surface of the solid phase if working in a heterogeneous system.

In contradistinction thereto, the present invention provides the possibility of also quantitatively determining the enzyme in the liquid phase in that the enzyme is used in a definite amount. In this way, for example, the carrying out of the whole test is possible in an extremely simple way in test tubes. Thus, for example, the complete antibody used can be bound adsorptively on the inner surface of a synthetic resin reagent glass or in the tray of a titer plate made of a synthetic resin, such as polystyrene, a solution is then introduced which contains the conjugate according to (c), the enzyme according to (d) and the sample solution (a). After termination of the incubation, the liquid phase is removed and the enzyme activity contained therein is measured as a measure of the amount of substance to be determined.

According to another embodiment, as solid phase-bound antibody (b) there can be used an antibody bound by ionic binding, immune precipitation or covalently on to a fleece to which is added the above-mentioned reaction components and, after termination of the incubation, again withdrawn by physical methods, for example by capillary force or centrifugal force.

As antienzyme-antibody-Fab fragments, there are preferably used those which do not influence the activity of the enzyme, i.e. neither activate nor inhibit. However, partly inhibiting or activating fragments can also be used.

When carrying out the process according to the present invention, the conjugate according to (c) and the enzyme according to (d) can be added separately to the determination batch. Alternatively, however, it is also possible to use the reactants (c) and (d) as a pre-mixture.

The present invention also provides a reagent for the determination of an immunologically bindable substance, which contains a solid phase-bound antibody against the bindable substance to be determined, a conjugate of the bindable substance to be determined and a Fab fragment of an antibody directed against a determinable enzyme, a determinable enzyme which binds immunologically with the Fab fragment contained in the conjugate and buffer.

The reagent according to the present invention preferably contains a system for the determination of the enzyme activity.

With regard to the solid phase-bound antibody, the conjugate and the enzyme, there applies, in the same way, that stated above in the statements made with regard to the process. The selected buffer is, in the first place, determined by the particular enzyme employed and is to be so chosen that, with regard to concentration and pH value, favourable conditions are present for the activity of the enzyme. These conditions and the appropriate buffer and buffer concentration are well known and do not need to be explained here in more detail.

The system for the determination of the enzyme activity depends, in turn, upon the enzyme used. The commercially available enzyme determination reagents which are available in large number and variety can be used for this purpose. When using peroxidase, as a rule, there is utilised the oxidation catalyzed by this enzyme in presence of hydrogen peroxide and there is used a system for the determination of this reaction.

If β-galactosidase is used as enzyme, then the system for the determination of its activity preferably consists of a galactoside with a group which can easily be determined optically, for example nitrophenylgalactoside, dinitrophenylgalactoside, aminophenylgalactoside or the like.

As solid phase, the reagent according to the present invention preferably contains a synthetic resin test tube or a synthetic resin plate with antibodies bound adsorptively on the surface. Another preferred solid phase-bound antibody consists of a fleece, for example a paper, on which the antibody is present, fixed according to one of the above-described methods.

By means of the present invention, it is achieved that, in the case of an immunochemical determination in heterogeneous phase with the use of an enzyme labelling, a native enzyme can be used and no previous binding on to another substance is needed. In the case of the previously necessary hapten/antigen-enzyme conjugates, in the course of the affinity chromatographic purification, as a rule, the enzyme activity is substantially destroyed by the elution conditions. In the case of the present invention, however, the necessary conjugates, since they do not contain any enzyme, can be brought to 100% immune reactivity by hapten-specific or antigen-specific affinity chromatographic purification.

The following Example is given for the purpose of illustrating the present invention:

EXAMPLE

Determination of T4 (thyroxine)

Reagents

β-galactosidase from *Escherichia coli*
 5 mg./ml.
 30 U/mg.
T4-conjugate with anti-β-galactosidase-antibody-Fab fragment, bound with the use of N-t.-butoxycarbonyl-tyroxyl-0-succinimide
 0.88 mg./ml.
 $\triangleq$ 164 mU/ml.
anti-T4-antibody bound adsorptively to the inner walls of polystyrene test tubes
Sincubation buffer
magnesium chloride
monosodium dihydrogen phosphate

Preparation of the solutions (1) incubation buffer is dissolved in 100 ml. double distilled water
(2) 100 μl. conjugate solution are dissolved in 25 ml. incubation buffer
(3) substrate buffer: 2 mM magnesium chloride, 100 mM monosodium dihydrogen phosphate (pH 7.2)
(4) substrate: 100 mg. nitrophenylgalactoside in 200 ml. substrate buffer
(5) 30 μl. β-galactosidase dissolved in 3 ml. of 2.2 M ammonium sulphate (pH 6)=1.5 U/ml.
(6) 0.5 ml. solution 5+20 ml. substrate buffer are mixed=37.5 mU/test.

Carrying out of the determination

100 μl. T4 standard and 1 ml. of solution 2 are pipetted into the synthetic plastic test tubes. They are then left to stand to incubate for 1 hour, thereafter the liquid is sucked out, the test tubes are rinsed with tap water and again sucked out. Subsequently, 1 ml. of solution 6 is introduced, again left to stand for 1 hour and sucked out, rinsed and again sucked out as described above. Thereafter, 1 ml. of substrate solution 4 is added and, after 30 minutes, the extinction is measured at 405 nm against the substrate buffer.

We claim:

1. A process for determining an immunologically bindable substance comprising:
   (a) incubating a liquid sample solution containing the substance to be determined with a solid phase antibody against the bindable substance to be determined, which solid phase antibody is present in an amount insufficient to bind all of said bindable substance, a conjugate of the bindable substance to be determined and an Fab fragment of an antibody directed against a determinable enzyme, said conjugate being present in a predetermined amount and a sample of said determinable enzyme,
   (b) separating said solid and liquid phases, and
   (c) measuring the enzyme activity in one of the two phases as a measure of bindable substance in said liquid sample.

2. The process of claim 1, wherein a predetermined amount of the determinable enzyme is used and the enzyme activity is measured in the liquid phase.

3. The process of claim 1 wherein the antibody against the bindable substance is bound to the solid phase adsorptively, covalently by polymerising or by cross-linking.

4. The process of claim 1 wherein the determinable enzyme is β-galactosidase or peroxidase.

5. The process of claim 1 wherein the Fab fragment is a monoclonal Fab fragment.

6. The process of claim 1 wherein the determinable enzyme is β-galactosidase and the enzyme is determined colorimetrically using a measuring system comprising nitrophenylgalactoside, dinitrophenylgalactoside or aminophenylgalactoside.

* * * * *